United States Patent
van Spronsen

(10) Patent No.: US 11,174,523 B2
(45) Date of Patent: Nov. 16, 2021

(54) RECOVERY OF LACTOSE FROM AN AQUEOUS SOLUTION

(71) Applicant: COOL SEPARATIONS B.V., Poortugaal (NL)

(72) Inventor: Jacob van Spronsen, Delft (NL)

(73) Assignee: Cool Separations B.V., Poortugaal (NL)

( * ) Notice: Subject to any disclaimer, the term of this patent is extended or adjusted under 35 U.S.C. 154(b) by 367 days.

(21) Appl. No.: 16/309,602

(22) PCT Filed: Jun. 13, 2017

(86) PCT No.: PCT/NL2017/050390
§ 371 (c)(1),
(2) Date: Dec. 13, 2018

(87) PCT Pub. No.: WO2017/217842
PCT Pub. Date: Dec. 21, 2017

(65) Prior Publication Data
US 2019/0144955 A1    May 16, 2019

(30) Foreign Application Priority Data
Jun. 13, 2016    (NL) .................................... 2016952

(51) Int. Cl.
*C13K 5/00*    (2006.01)
*C07H 3/04*    (2006.01)
(Continued)

(52) U.S. Cl.
CPC .............. *C13K 5/00* (2013.01); *B01D 9/0063* (2013.01); *B01D 9/04* (2013.01); *C07H 1/06* (2013.01); *C07H 3/04* (2013.01); *A23C 21/00* (2013.01)

(58) Field of Classification Search
None
See application file for complete search history.

(56) References Cited

U.S. PATENT DOCUMENTS

| 6,077,358 A * | 6/2000 | Giersch | C13B 30/005 |
| | | | 106/151.1 |
| 2006/0128953 A1* | 6/2006 | Shi | C07H 3/04 |
| | | | 536/123.13 |

(Continued)

FOREIGN PATENT DOCUMENTS

| CN | 102516321 A | * | 6/2012 |
| EP | 1094047 A1 | | 4/2001 |
| WO | WO 2013/051935 A1 | | 4/2013 |

OTHER PUBLICATIONS

CN-102516321-A—English translation (Year: 2011).*

(Continued)

*Primary Examiner* — Stefanie J Cohen
(74) *Attorney, Agent, or Firm* — BakerHostetler

(57) ABSTRACT

The invention is directed to a method for recovering lactose from an aqueous lactose solution comprising a concentration step, wherein water is removed from the aqueous lactose solution by freezing out water at a temperature below the eutectic temperature of the aqueous lactose solution and at a lactose concentration higher than the eutectic concentration of the aqueous lactose solution, thereby obtaining a concentrated lactose solution; and a crystallization step, wherein at least part of the concentrated lactose solution is subjected to crystallization at a temperature above the eutectic temperature of the concentrated lactose solution, thereby obtaining lactose crystals.

15 Claims, 3 Drawing Sheets

(51) Int. Cl.
    *C07H 1/06*    (2006.01)
    *B01D 9/00*    (2006.01)
    *B01D 9/04*    (2006.01)
    *A23C 21/00*   (2006.01)

(56) References Cited

U.S. PATENT DOCUMENTS

2014/0341934 A1* 11/2014 van Spronsen .... B01D 11/0288
                                                    424/184.1
2014/0374361 A1* 12/2014 van Spronsen ........... C02F 5/02
                                                    210/712

OTHER PUBLICATIONS

Van der Ham et al., "Eutectic Freeze Crystallization: Application to process streams and waste water purification", Chemical Engineering and Processing, 1998, 37, 207-213.

* cited by examiner

RECOVERY OF LACTOSE FROM AN AQUEOUS SOLUTION

CROSS-REFERENCE TO RELATED APPLICATIONS

This application is the National Stage of International Patent Application No. PCT/NL2017/050390, filed Jun. 13, 2017, which claims priority from Netherland Patent Application No. 2016952, filed Jun. 13, 2016, the disclosures of which are incorporated herein by reference in their entireties for any and all purposes.

The invention is directed to a method for recovering lactose from an aqueous lactose solution, in particular from a whey permeate. The invention is further directed to a mixture of ice crystals and an aqueous lactose solution.

Lactose is a disaccharide sugar derived from galactose and glucose, which compound is found in milk. Lactose is industrially produced from whey, which is the liquid remaining after milk has been curdled and strained. The composition of whey may vary, but generally comprises lactose (typically about 5 wt. %), whey protein (typically about 1 wt. %), ash (typically about 0.5 wt. %) organic acids such as citric acid and lactic acid and some minerals and vitamins. Whey protein (which mainly consists of α-lactalbumin and ß-lactoglobulin) is used as a nutritional supplement in for example infant nutrition and sport nutrition.

Methods for recovering whey protein and lactose from whey are well known in the art. In these known methods, whey is subjected to filtration (e.g. ultrafiltration or microfiltration), which results in a retentate comprising whey protein and a permeate comprising lactose (herein also referred to as the "whey permeate"). Whey protein can be isolated from the retentate, while lactose can be isolated from the permeate. The permeate obtained by ultrafiltration step has a lactose concentration of about 5 wt. %. The permeate may further comprise other water soluble compounds that were present in the whey, such as citric acid and phosphoric acid. The permeate is concentrated by evaporation to a concentration close to the saturation point of lactose, which corresponds to a concentration of about 60-70 wt. % lactose. The concentration step is conducted at an elevated temperature of about 80-100° C., typically under reduced pressure. Subsequently, lactose is recovered by crystallization by slowly cooling the concentrated permeate from elevated temperature to room temperature. The solid crystals are removed, e.g. by filtration. The mother liquor that remains after the crystallization step may be referred to as the 'delactosed whey permeate'.

A disadvantage of the method of the prior art is that the mother liquor remaining after crystallization still comprises a significant amount of lactose. Due to high energy consumption of evaporation, it is generally not economically viable to subject the mother liquor to a second concentration and crystallization step. Accordingly, about 30% of the total lactose present in the whey permeate is not recovered.

Although it is in theory possible to recover further lactose from the delactosed whey permeate, the costs for doing so are generally considered not worth it, for example due to the complexity of the recovery steps, expensive equipment and/or high energy consumption.

WO 2014/141164 describes a method for recovering lactose from a lactose containing liquid source (e.g. a permeate from filtration of milk or whey). The document describes that lactose crystallization is typically carried out by first concentrating the lactose in the solution to become super saturated (e.g. by evaporation or reverse osmosis) followed by controlled cooling and inducing crystal growth in a cooling crystallizer. Crystals are then extracted from the liquid, yielding raw lactose and a lactose-containing liquid stream (mother liquor). WO 2014/141164 provides a method for further recovery of lactose, wherein the obtained lactose-containing liquid stream is subjected to an optional step of heating and/or pH adjustment, a first step comprising filtration or ultrafiltration and a second step comprising nanofiltration. The extract obtained in the nanofiltration step may be added to the lactose-containing liquid source before, during or after entry into the crystallization process. The method of WO 2014/141164 is said to reduce the amount of lactose lost as waste.

A disadvantage of the method described in WO 2014/141164 is that high temperatures are need for conducting the concentration step. Not only does this result in a high energy consumption, but it may also promote degradation reactions that negatively affect the final lactose yield.

An object of the invention is to provide an energy efficient method for recovering lactose from an aqueous lactose solution.

It is a further object to provide an energy efficient method for recovering lactose with which a more complete recovery is obtained compared to methods known in the prior art.

In particular, it is an object of the invention to provide a method with which more than 90% of the total lactose present in a whey permeate can be recovered, while consuming less energy than the recovery methods known in the art.

At least one of these objects was met by providing a method for recovering lactose from an aqueous lactose solution comprising
  a concentration step, wherein water is removed from the aqueous lactose solution by freezing out water at a temperature below the eutectic temperature of the aqueous lactose solution and at a lactose concentration higher than the eutectic concentration of the aqueous lactose solution, thereby obtaining a concentrated lactose solution; and
  a crystallization step, wherein at least part of the concentrated lactose solution is subjected to crystallization, preferably at a temperature above the eutectic temperature of the concentrated lactose solution, thereby obtaining lactose crystals.

The inventors surprisingly found that it was possible to concentrate a lactose solution beyond its eutectic concentration by freezing water out of the lactose solution. No significant amount of lactose was crystallized at the eutectic concentration of lactose when cooling a lactose solution below the eutectic temperature, at least not until the lactose solution was cooled well below −2° C. Accordingly, the inventors realized that it was possible to concentrate the lactose solution by freezing the solvent (water) and removing ice from the lactose solution. This was unexpected considering that the eutectic point of a lactose in water solution lies at a temperature of −0.65° C. at a concentration of 10 wt. %, based on the total weight of the lactose in water solution. In view of the eutectic point, one would thus expect that lactose and ice would simultaneously start to crystallize once the eutectic point was reached, such that lactose concentration of the solution would be maintained at 10 wt. %, based on the total weight of the solution. If this had been the case, no efficient concentration could have been achieved. However, the inventors found that lactose does not behave normally at the eutectic point. Instead of lactose and water simultaneous crystallizing at the eutectic point, only water will crystallize, while no significant amounts of lactose crystals are formed when the eutectic point is reached. The inventors found that by freezing out water in this way, a lactose concentration of 27 wt. % could be achieved. However, the inventors expect that lactose solutions can be obtained with an even higher lactose concentration.

Although the technique of eutectic freeze crystallization is known from e.g. WO 2013/051935 and EP 1 094 047, it has never been suggested to cool a solution below its eutectic temperature for concentrating lactose solutions. It would be expected that applying EFC would result in a significant decrease in lactose yield.

Without wishing to be bound by any theory, the inventors believe that both the rate of nucleation of lactose crystals and the rate at which lactose molecules attach to the crystal nucleus (causing it to grow) are very low. As a result, crystallization of lactose does not immediately occur when cooling an aqueous lactose solution to a temperature below 0° C., not even when the concentration of lactose in the aqueous lactose solution is higher than the eutectic concentration. Thus, it is possible to concentrate lactose solutions by crystallizing water before significant amounts of lactose crystals form.

An advantage of the method of the invention is that the concentration step is very energy efficient, especially compared to concentration steps based on evaporation. The amount of energy required for bringing water from liquid state to gaseous state (enthalpy of evaporation) is much larger than the amount of energy required for bringing water from liquid state to solid state (enthalpy of sublimation).

A further advantage is that the method of the invention does not make use of high temperatures, such that any temperature sensitive compounds that may be present in the aqueous lactose solution are not damaged or degraded.

A further advantage is that the method of the invention is that it is easy to conduct with only a small amount of process steps. Further, the method of the invention does not require any expensive equipment.

The eutectic point is a physical property of a salt/water mixture that is well-known in the art. It refers to a characteristic point in the phase diagram of a salt/water mixture. At the eutectic point an equilibrium exists between ice, salt crystals and a salt solution with a specific concentration. This specific concentration is called the eutectic concentration and the temperature at which this equilibrium is found is the eutectic temperature. Salt and water will simultaneously crystallize at the eutectic point. Although the eutectic point is mostly described for salts in the art, a similar point exists for mixtures of organic compounds (such as lactose) and water.

Figure 1:
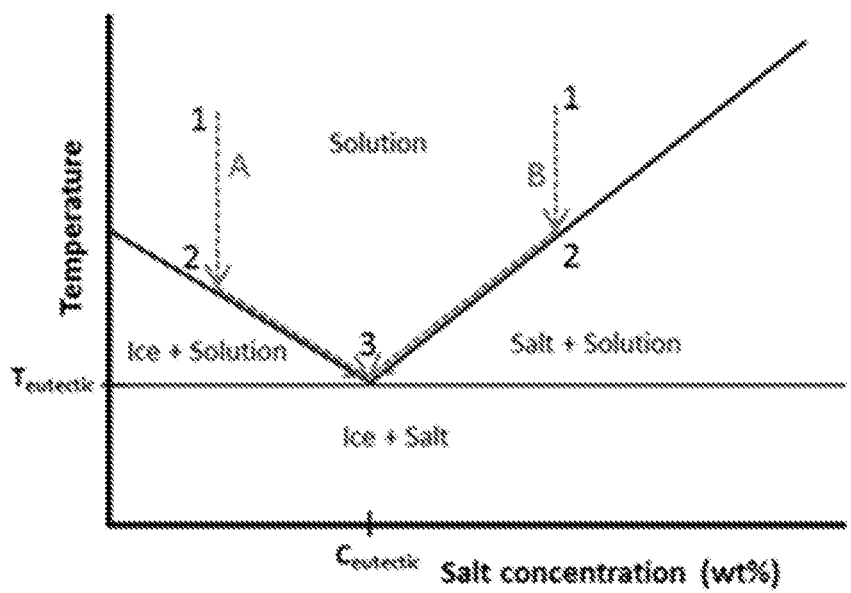
FIG. 1 shows a typical phase diagram for salt-water system showing the eutectic point, wherein the x-axis represents the salt concentration (in wt. %) and the y-axis represents the temperature (in ° C.).
Figure 2:
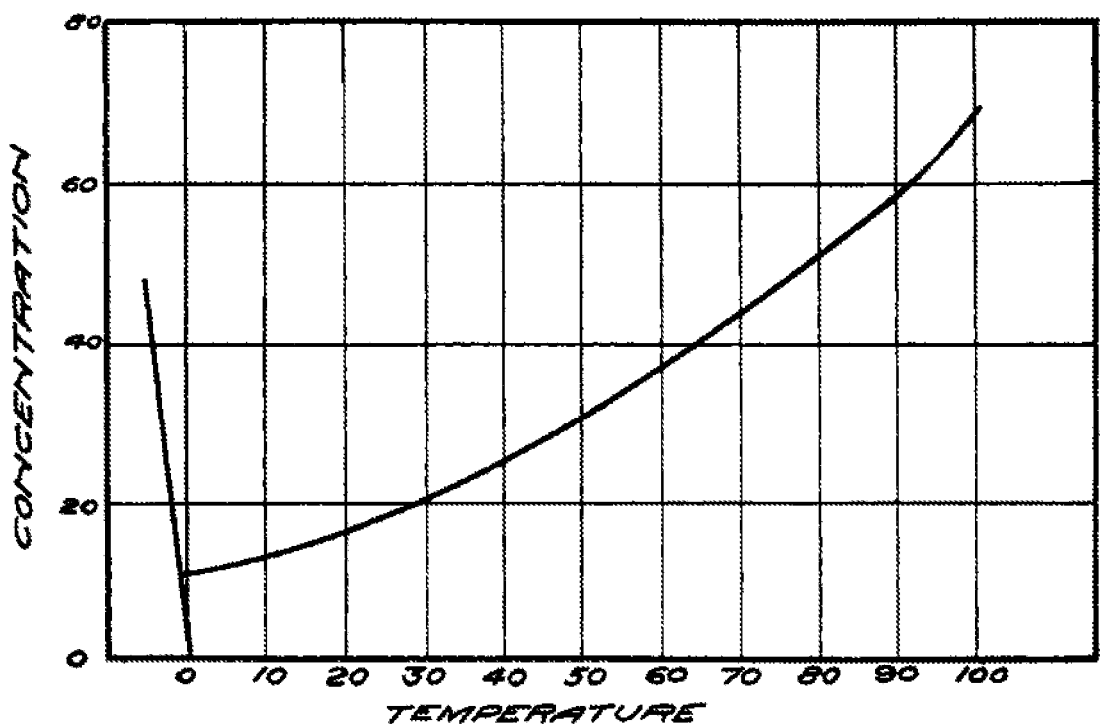
FIG. 2 shows the phase diagram for a lactose/water mixture showing the eutectic point, wherein the x-axis represents the temperature (in ° C.) and the y-axis represents the lactose concentration (in wt. %). The eutectic point is the point in the phase diagram wherein the water and lactose lines intersect.

Referring to FIG. 1, the behavior of a typical salt/water mixture can be described as follows. In the case that an aqueous solution has exactly the eutectic concentration, cooling the solution down towards its eutectic temperature will lead to the simultaneous crystallization of both ice and salt. However, in practice it is common that a solution has a salt concentration that is lower or higher than the eutectic concentration. In the former case ice will crystallize first (point 2) when the temperature is decreased. Due to the formation of ice the salt concentration in the remaining liquid (the mother liquor) increases, which leads to a decrease in freezing point and by continued cooling the ice line is followed till the eutectic point (3) is reached. This is represented by path A in FIG. 1. When the original salt concentration is higher than the eutectic concentration the opposite happens (path B); first salt is crystallizing (2) till the salt concentration of the mother liquor decreases to the eutectic concentration, from that moment on also ice will be formed (3). The locations of the eutectic points in a water-salt mixture is dependent on the type of ions in solution and can vary over a broad range (both in temperature as well as concentrations) for different systems.

The term "eutectic point" as used herein refers to a characteristic point in the phase diagram of the lactose/water mixture used in the invention (i.e. of the aqueous water solution). In particular, the eutectic point refers to the temperature/concentration point at which an equilibrium exists between ice, lactose crystals and a lactose in water solution. The specific lactose concentration at this point is called the eutectic concentration and the temperature at which this equilibrium is found is the eutectic temperature.

The eutectic point of a lactose/water mixture lies at a lactose concentration of 10 wt % (based on the total weight of the mixture) at a temperature of −0.65° C. The eutectic point of a lactose/water mixture is known in the art, for example from the scientific publication by C. S. Hudson in *J. Am. Chem. Soc.*, 1908, 30 (11), pp 1767-1783. The eutectic point can be determined as explained in Example 1 further below.

The method of the invention is described in more detail below.

The lactose solution is an aqueous solution of lactose in water. The lactose solution may further comprise organic acids, such as citric acid, phosphoric acid and lactic acid. When present, the concentration of organic acid in the solution is typically small, e.g. less than 1 wt. % or even less than 0.5 wt. % based on the total weight of the solution. However, concentrations higher than 1 wt. % are also possible. Generally, the acidity of the solution has no negative effect on crystallization.

The lactose solution may further comprise minerals and vitamins. The lactose solution is preferably a whey permeate or a delactosed whey permeate. A whey permeate can be obtained by filtration of whey, as described above.

The lactose concentration in the initial lactose solution, i.e. prior to the concentration step, may be 1-25 wt. %, typically 1-15 wt. %, preferably 2-10 wt. % e.g. 3-8 wt. % lactose based on the total weight of the initial lactose solution. The lactose concentration in whey permeate is typically around 5 wt. %. The lactose concentration of delactosed whey permeate can be as high as 15 wt and is generally within the range of 5-18 wt. %.

As used herein, the term "lactose solution" refers to an aqueous solution comprising dissolved lactose and optionally other dissolved material. The term may also refer to the liquid part of a slurry or mixture of lactose solution and crystals (e.g. ice crystals and/or lactose crystals).

In the concentration step, the lactose solution is cooled to a temperature below the eutectic temperature of the aqueous lactose solution (which temperature lies below 0° C.), such that part of the water of the lactose solution is frozen to form ice crystals. The ice crystals are removed from the lactose solution, such that a concentrated lactose solution is obtained. Ice crystals can be easily separated from the lactose solution based on their difference in density, for example by filtration.

In particular, the concentration step is conducted at a temperature below the eutectic temperature of the lactose solution. The inventors found that no significant amount of lactose was crystallized below the eutectic temperature of the lactose solution, at least not until the lactose solution was cooled well below −2° C. Preferably, the concentration step is conducted at a temperature 0.5-20° C. below the eutectic temperature, more preferably 1-15° C. below the eutectic temperature, even more preferably 2-12° C. below the eutectic temperature, for example 3-10° C. below the eutectic temperature of the lactose solution. The inventors found that no significant amount of lactose would crystallize, even at temperatures that were more than several degrees below the eutectic temperature. It was further found that water would more rapidly crystallize at such low temperatures, which is desirable for the efficiency of the concentration step.

The concentration step may be conducted at a temperature of −1 to −21° C., preferably −2 to −16° C., more preferably −3 to −13° C., for example −4 to −11° C. The concentration step may even be conducted at temperatures below −5 or even below −8° C.

The lactose concentration of the aqueous lactose solution is increased during the concentration step to a concentration that is higher than the eutectic concentration. The lactose concentration may be increased to a concentration of at least 5. wt % above the eutectic concentration, preferably at least 15 wt. % above the eutectic concentration, more preferably at least 25 wt. % above the eutectic concentration or even at least 40 wt. % above the eutectic concentration, based on the total weight of the lactose solution. For example, the lactose concentration is increased to a concentration of at least 15 wt. %, preferably at least 25 wt. %, more preferably at least 40 wt. % or even at least 50 wt. %, based on the total weight of the lactose solution.

The concentration step may be conducted in a first crystallizer. The first crystallizer may be a crystallizer suitable and/or designed for crystallization below 0° C., such as a freeze crystallizer or an Eutectic Freeze Crystallization (EFC) Crystallizer. Preferably, the concentration step is conducted continuously. However, it is also possible to conduct the concentration step batch-wise.

Typically, the concentration step results in two streams. The first stream is an ice stream, while the second stream is a concentrated lactose solution. The ice stream comprises solid ice crystals and typically further comprises part of the lactose solution (in which case it may also be referred to as the ice crystal slurry). The ice crystals are discarded, while the lactose solution can be fed back to the first crystallizer. Before discarding the ice crystals, they may be washed, e.g. with water. Any washing water may be fed back to the first crystallizer. However, one should be careful to feed back too much washing water as this will dilute the system, which may result in a less effective concentration step.

The formation of lactose crystals in the concentration step is generally considered undesirable. Accordingly, preferably more than 95 wt. %, more preferably more than 99 wt. %, even more preferably more than 99.5 wt. %, even more preferably more than 99.9 wt. % of lactose is in dissolved form during the concentration step. Furthermore, preferably, less than 5 wt. %, more preferably less than 1 wt. %, even more preferably less than 0.5 wt. %, even more preferably less than 0.1 wt. % of the crystals formed in the concentration step are lactose crystals, based on the total weight of crystals formed. In view of the above, it will be evident that the concentration step is typically conducted in the absence of lactose seed material.

Although it may not be desirable, it is possible that some amount of lactose crystals form in the concentration step. However, this does not have to have a negative impact on the efficiency of this step. Typically, lactose crystal formed in the concentration step is removed together with the ice crystals before the lactose crystal had had much time to grow. This is particularly the case for a concentration step that is conducted continuously. In a continuous concentration step, there is a constant stream of crystals removed from the lactose solution. Accordingly, even in case small amounts of lactose crystals would be formed, these would be quickly removed from the lactose solution. As a result, even if a lactose crystal is formed, it will not grow to a significant size. Also, in case the method of the invention comprises a washing step, any lactose crystal formed may end up in the washing water (in dissolved form) and may be fed to the lactose solution which is fed back to the first crystallizer. Accordingly, formation of lactose crystals in the crystallization step does not have a negative impact the lactose yield.

In a specific embodiment of the embodiment, lactose is simultaneously crystallized with water in the concentration step. Such simultaneous crystallization is generally not considered desirable, because it either results in the loss of lactose (when discarded together with the ice crystals) or requires an additional separation step to recover lactose crystals. Nevertheless, this embodiment may be a viable method to concentrate the aqueous lactose solution beyond its eutectic concentration. In case of an additional separation step, lactose crystals and ice crystals may in this case be separated from each other based on their difference in density. In this specific embodiment, the concentration step may be a eutectic freeze concentration step or the concentration step may be a combination of at least one 'regular' concentration step and at least one eutectic freeze crystallization step.

The concentration step is conducted in order to obtain a concentrated solution having a lactose concentration of at least 15 wt. %, preferably at least 25 wt. %, more preferably at least 40 wt. % lactose, based on the total weight of the lactose solution.

At least part of the concentrated lactose solution is subjected to the crystallization step. The at least part of the concentrated lactose solution preferably has a lactose concentration prior to the crystallization step of at least 15 wt. %, more preferably at least 25 wt. %, more preferably at least 40 wt. %. In order to promote crystallization, seed crystals may be provided to the solution.

In the crystallization step, the concentrated lactose solution is subjected to crystallization. The crystallization step is conducted at a temperature above the eutectic temperature of the concentrated lactose solution, typically at a temperature of 0° C. or higher. If necessary, the concentrated lactose solution obtained in the concentration step (conducted at <0° C.) may first be brought to a temperature above such a temperature. Since the temperature of the concentrated lactose solution is typically about 0° C. after filtration, it is not required to conduct a separate heating step. However, when conducting the crystallization step at a temperature higher than 0° C., the method may comprise a heating step prior to the crystallization step (and after the concentration step) in order to increase the temperature of the concentrated lactose solution to its desirable value.

Crystallization may be conducted at relatively low temperatures, typically below 20° C. A low crystallization temperature is desirable, because the solubility of lactose increases at higher temperature, such that the lactose yield decreases when conducting crystallization at higher temperatures. For this reason, a crystallization temperature below 10° C., for example below 5° C. or even below 3° C. may be preferred.

On the other hand, the crystallization temperature is preferably not too low. In order to obtain crystals with good quality (e.g. crystal size) and purity, crystallization is preferably conducted at a temperature of at least 2° C. or at least 4° C. or at least 6° C. An additional advantage of using a crystallization temperature higher than 0° C. is that it increases the rate of crystallization, thus speeding up the process.

Preferably, lactose seed material is added to the concentrated lactose solution. Crystallization in the presence of lactose seed crystals may promote the nucleation and growth of the lactose crystals, which is desirable in view of the low nucleation and growth rates observed for these crystals.

The crystallization step is typically conducted in a second crystallizer. In view of the different crystallization conditions required, the concentration step and crystallization step are preferably conducted in separate crystallizers. The crystallization step results in lactose crystals and a mother liquor.

The method of the invention may further comprise an isolation step, wherein the lactose crystals formed in the crystallization step are separated from the mother liquor. This may be done by any suitable method known in the art e.g. by filtration. The mother liquor may still comprise certain amounts of lactose and may be fed back to the crystallizer of the concentration step.

In case organic acids are present in the aqueous lactose solution, the filtrate obtained in the isolation step may be subjected to a further step to recover one or more organic acids, for example citric acid.

Preferably, the crystallization and isolation steps are conducted continuously. However, it is also possible to conduct the crystallization and isolation step batch-wise. More preferably, the method of the invention is conducted continuously. Nevertheless, it is also possible to conduct the method batch-wise.

In case of a continuous method, the aqueous lactose solution may also be referred to as the aqueous lactose stream. This stream may be fed to a first crystallizer wherein ice crystals are formed. The concentration step results in at least two streams: a concentrated lactose stream comprising lactose and liquid water; and an ice crystal stream, which typically is a slurry of ice crystals in lactose solution. The ice crystals are removed from the ice crystal stream, e.g. by filtration. The ice crystals may be washed, e.g. with water. The liquid part of the ice crystal stream and optionally the washing water may be fed back to the aqueous stream. At least part of the lactose stream is fed to a second crystallizer, wherein lactose is crystallized. This step results in lactose crystals and a mother liquor. The part of the lactose stream that is not fed to the crystallizer is typically fed back to the aqueous stream. Also, the mother liquor may be fed back to the aqueous stream.

Figure 3:
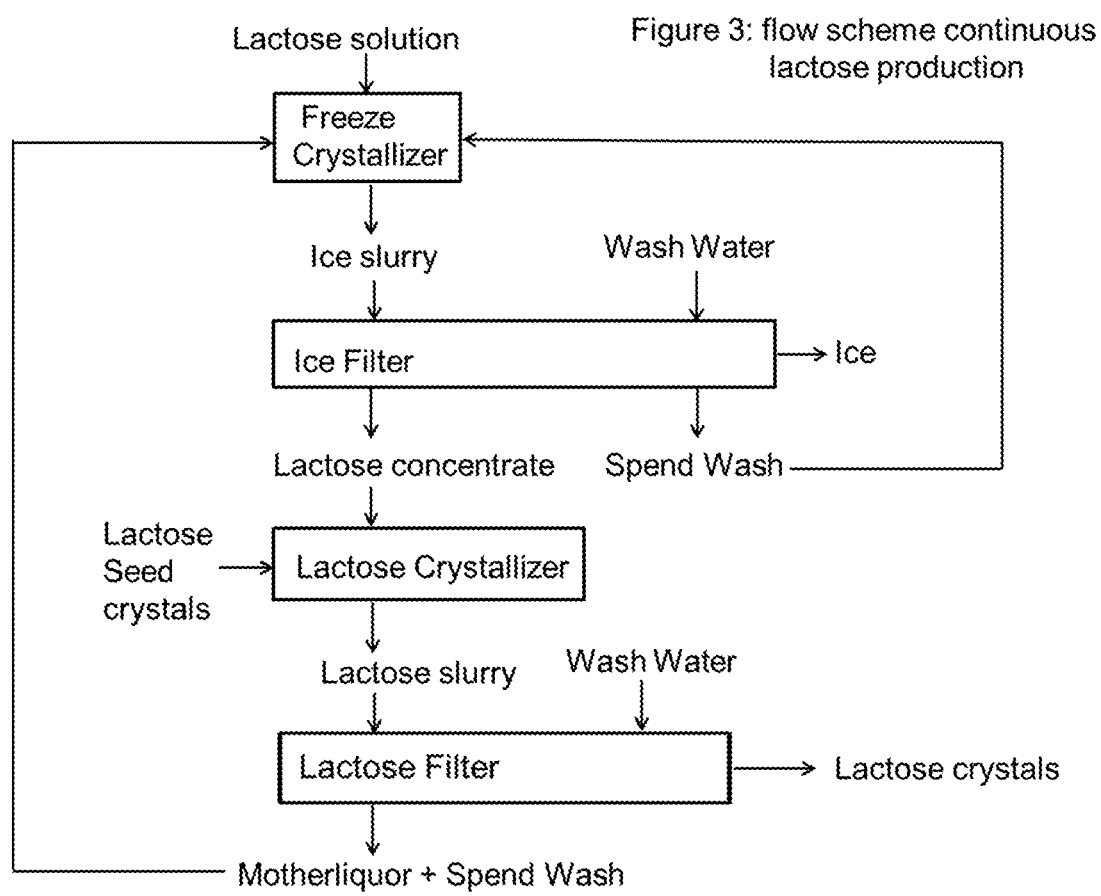
FIG. 3 shows a schematic representation of one embodiment of the method of the invention.

An example of a continuous method according to the invention is shown in FIG. 3. A lactose solution is fed to a freeze crystallizer, which results in an ice slurry which is separated into two streams by an ice filter: (i) ice and (ii) a concentrated lactose solution (called lactose concentrate in FIG. 3). The ice is washed with water; the ice is removed from the system, while the washing water is fed back to the freeze crystallizer. The lactose concentrate is fed to a lactose crystallizer with lactose seed crystals, wherein lactose is crystallized and thus a lactose slurry of mother liquor and lactose crystals obtained. A lactose filter is used to separate the mother liquor from the lactose crystals. The crystals are washed with water. The mother liquor and washing water are fed back to the freeze crystallizer.

The invention is further directed to a mixture of ice crystals and an aqueous lactose solution, wherein the lactose solution has a lactose concentration above the eutectic concentration of the lactose solution. Such a mixture is obtained in the concentration step of the method of the invention. Accordingly, parameters regarding for example lactose concentration and the amount of lactose crystals described above for the concentration step also apply to the mixture of the invention.

ILLUSTRATIVE EMBODIMENTS

Provided here are illustrative embodiments of the disclosed technology. These embodiments are illustrative only and do not limit the scope of the present disclosure or of the embodiments attached hereto.

Embodiment 1. A method for recovering lactose from an aqueous lactose solution, the method comprising (a) concentrating the aqueous lactose solution, wherein water is removed from the aqueous lactose solution by freezing out water at a temperature below the eutectic temperature of the aqueous lactose solution and at a lactose concentration higher than the eutectic concentration of the aqueous lactose solution, thereby obtaining a concentrated lactose solution; and (b) a crystallizing the lactose, wherein at least part of the concentrated lactose solution is subjected to crystallization at a temperature above the eutectic temperature of the concentrated lactose solution, thereby obtaining lactose crystals.

Embodiment 2. The method according to embodiment 1, wherein the water is removed from the aqueous lactose solution at a lactose concentration higher than 15 wt. %, preferably higher than 25 wt. %, based on the total weight of the aqueous solution.

Embodiment 3. The method according to any of the previous embodiments, wherein the water is removed from the aqueous lactose solution by cooling to a temperature that lies 1-20° C., preferably 1-15° C., more preferably 2-10° C. below the eutectic temperature of the aqueous mixture.

Embodiment 4. The method according to any of the previous embodiments, wherein the crystallization of the lactose in (b) is conducted at a temperature of at least 0° C.

Embodiment 5. The method according to any of the previous embodiments, wherein the concentration of the aqueous lactose solution in (a) is conducted at a temperature below −1° C. and the crystallization step is conducted at a temperature of at least 0° C.

Embodiment 6. The method according to any of the previous embodiments, wherein the concentration of the aqueous lactose solution in (a) is conducted to obtain a concentrated solution having a lactose concentration of at least 15 wt. %, preferably at least 20 wt. %.

Embodiment 7. The method according to any of the previous embodiments, wherein the method is a continuous method.

Embodiment 8. The method according to any of the previous embodiments, wherein the aqueous solution originates from a whey permeate obtained by filtration of whey.

Embodiment 9. The method according to any of the previous embodiments, wherein more than 99.9 wt. % of lactose is in dissolved form during the concentration of the aqueous lactose solution in (a).

Embodiment 10. The method according to any of embodiments 1-8, wherein the concentration of the aqueous lactose solution in (a) is a eutectic freeze crystallization step Embodiment 11. A mixture-of ice crystals and an aqueous lactose solution produced by freezing out water at a temperature below the eutectic temperature of the aqueous lactose solution and at a lactose concentration higher than the eutectic concentration of the aqueous lactose solution, wherein the aqueous lactose solution has a lactose concentration higher than 15 wt. %, preferably higher than 25 wt. %, based on the total weight of the aqueous lactose solution.

The invention is illustrated by the following examples.

EXAMPLE 1: DETERMINING THE EUTECTIC POINT

The eutectic point of a lactose solution can be determined as follows.

A lactose solution containing ice and lactose crystals is prepared. An excess of lactose is added to the solution, so that lactose is both present in dissolved and crystallized form. Due to the presence of lactose crystals, the effects of slow nucleation will be negated and lactose may crystallize upon the already existing lactose crystals.

The solution is cooled down until ice crystals are formed. Preferably, ice seed crystals are used to promote crystallization of ice.

The resulting slurry is stirred and the temperature is kept as constant as possible after the first ice crystals are formed (i.e. close to/at the eutectic point). The lactose concentration is measured over time, for example each couple of hours. The three-phase system is maintained and the lactose concentration is measured until the lactose concentration is constant and does no longer change over time. This may take several days as the mutarotation of lactose is very slow at 0° C. The temperature and concentration at this point are the eutectic temperature and concentration of the system.

The eutectic point of a lactose/water mixture has been determined in the art in a similar way as described above. The eutectic point measured was −0.65° C. at a lactose concentration of 10 wt. %.

EXAMPLE 2: CONCENTRATION OF A LACTOSE SOLUTION

A saturated lactose solution was prepared by adding an excess amount of α-lactose monohydrate to 2 liters of water. After stirring for four days at room temperature the slurry was filtered over a glass filter. The lactose concentration in the solution was determined at 16%. 830 Grams of the saturated lactose solution was added to a crystallizer equipped with a stirrer, two temperature sensors and a cooling jacket. Under stirring the lactose solution in the crystallizer was cooled to −3.5° C. At this point ice started crystallizing and the temperature increased to −1.4° C. due to the released heat of crystallization. Upon further cooling the temperature slowly decreased to −2.5° C. and the crystallizer filled up with ice crystals without any lactose crystals present. The ice slurry was filtered over a glass filter. The filtrate was a clear solution. The lactose concentration in the filtrate was 27%. The filtrate was stirred overnight at room temperature leading to crystallization of lactose. After an additional 3 days stirring at room temperature the crystals were filtered over a glass filter. 29.8 g of α-lactose monohydrate was isolated (about 25% of the starting amount present in the 830 gram solution). The lactose concentration in the mother liquor after filtration was 19%.

EXAMPLE 3: CONTINUOUS CONCENTRATION OF A LACTOSE SOLUTION

In this example, a saturated lactose solution was concentrated using continuous concentration at a temperature below the eutectic temperature according to the invention and subsequently recovered by a concentration step conducted at a higher temperature.

Figure 4:
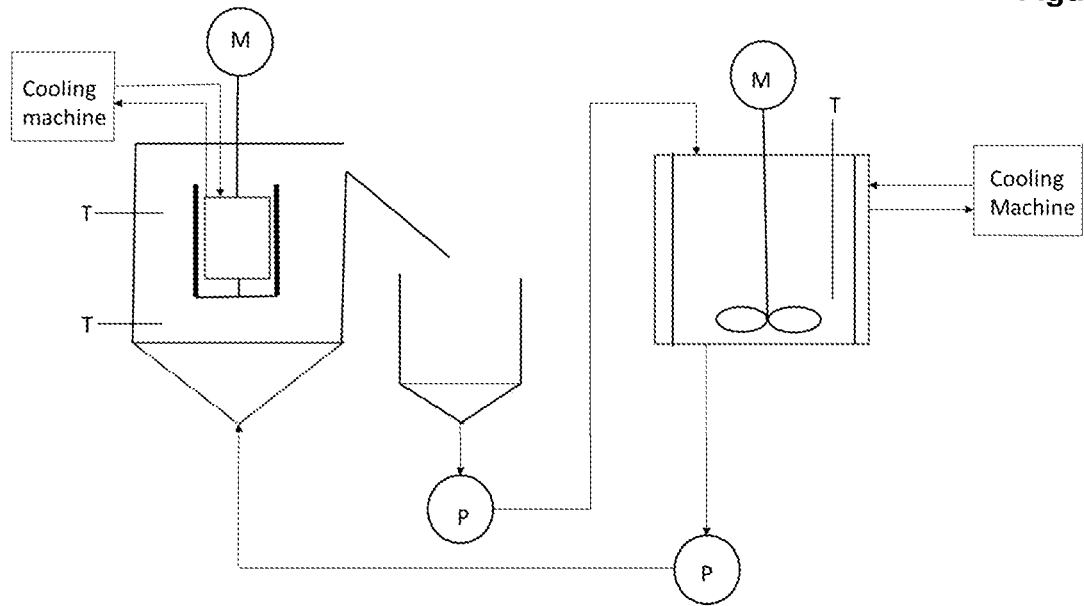
FIG. 4 shows the set up of the experiment for continuous concentration of a lactose solution.

The set up of the experiment consisted of a 10 liter isolated crystallizer equipped with a heat exchanger (scraped surface heat exchanger—SSHE) on the inside and two temperature sensors (T). The heat exchanger was connected to a cooling machine, such that the temperature of the crystallizer could be set to temperatures below the eutectic temperature. A Buchner filter was positioned such as to receive the overflow of the crystallizer into the filter. The Buchner filter was fluidly connected to a double walled isolated buffer vessel. A pump was installed to pump the filtrate from the Buchner filter to the vessel. The buffer vessel was equipped with a stirrer and a temperature sensor (T). The content of the buffer vessel could be kept at the required temperature with a cooling machine. Via the bottom outlet of the buffer vessel solution could be pumped back to the crystallization vessel. The set up is shown in FIG. 4.

A saturated lactose solution was prepared by dissolving 5.5 kg lactose monohydrate in 19 kg of hot water. The concentration of the solution was measured with a refractometer and was 21.2° Brix.

The buffer vessel was filled with the 24.5 kg lactose solution. The temperature in the buffer vessel was set at −2° C. The crystallizer was continuously fed from the buffer vessel with a flow rate of 20 litre per hour (generally, a flow rate of 1-50, preferably 5-30 litre per hour may be used in the continuous concentration step of the invention). At the moment the liquid in the crystallizer started to overflow into the Buchner filter, the cooling machine connected to the scraped surface heat exchanger was started and set to a temperature of −12° C. Also the second pump was started to pump the liquid from the Buchner filter to the buffer vessel at a pump rate of 20 litre per hour. After one hour of cooling, ice started collecting in the Buchner filter. Each time the Buchner filter was completely filled with ice, the ice was removed from the filter and the empty filter was placed back in the set up. After 5 hours of circulation, a brix of 33.3 was reached in the buffer vessel and 11.1 kg of ice was collected from the Buchner filter.

To 6.8 kg of the concentrated lactose solution obtained by the continuous concentration step described above, 20 grams lactose monohydrate seed crystals were added and the mixture was stirred for 17 hours at 15° C. After 17 hours of crystallization, the crystals were isolated by filtration over a glass filter. The concentration of lactose in the ML was 19.7° Brix after crystallization. The collected crystals were dried at the air until constant weight yielding 1.19 kg of lactose (50%, taking losses into account).

EXAMPLE 4: CONCENTRATION OF DELACTOSED PERMEATE (DLP)

In this example, the method of the invention is applied to recover lactose crystals from delactosed permeate.

An amount of 3.75 kg of delactosed whey permeate (25.1° Brix) was added to a 5 liter double walled crystallizer equipped with an agitator, a thermometer and connected to a cooling machine. Under stirring the content of the crystallizer was cooled below 0° C. After the crystallization of a sufficient amount of ice (making stirring difficult) the content of the crystallizer was filtered over a glass filter. The mother liquor (ML) was placed back into the crystallizer and the process above was repeated.

After three cycles of crystallization of ice and ice removal by filtration over a glass filter, the concentration process was continued in a 1 liter double walled crystallizer equipped with an agitator and a thermometer. After 2 cycles of crystallization of ice and ice removal, 0.58 kg of mother liquor remained with a Brix of 43.6°.

The results of the crystallization cycles are shown in Table 1.

TABLE 1

Concentration of delactosed permeate

| | °Brix | Concentration Factor | Volume Reduction [%] | Ice crystallization Temperature [° C.] |
|---|---|---|---|---|
| Start solution | 25.1 | 1 | | |
| 1$^{st}$ ML | 28.5 | 1.14 | 12.28 | |
| 2$^{st}$ ML | 31.3 | 1.25 | 20.00 | −6.45 |
| 3$^{nd}$ ML | 35.8 | 1.43 | 30.07 | −7.92 |
| 4$^{th}$ ML | 38.2 | 1.52 | 34.21 | −9.85 |
| 5$^{th}$ ML | 43.6 | 1.74 | 42.53 | −11.33 |

To the 0.58 kg of mother liquor 3 gram of lactose seed crystals were added. The resulting slurry was stirred for 17 hours at 15° C. The slurry was filtered over a glass filter. The lactose crystals were taken from the filter and dried on the air until constant weight yielding 55 gram (25%, taking losses into account).

This example shows that delactosed permeate can be concentrated in an efficient way beyond its eutectic concentration, resulting in an improved yield of lactose crystals in the subsequent crystallization step.

The invention claimed is:

1. A method for recovering lactose from an aqueous lactose solution, the method comprising:
    (a) concentrating the aqueous lactose solution, wherein water is removed from the aqueous lactose solution by freezing out water at a temperature below the eutectic temperature of the aqueous lactose solution and at a lactose concentration higher than the eutectic concentration of the aqueous lactose solution, thereby obtaining a concentrated lactose solution; and
    (b) crystallizing the lactose, wherein at least part of the concentrated lactose solution is subjected to crystallization at a temperature above the eutectic temperature of the concentrated lactose solution, thereby obtaining lactose crystals.

2. The method according to claim 1, wherein the water is removed from the aqueous lactose solution at a lactose concentration higher than 15 wt. %, based on the total weight of the aqueous solution.

3. The method according to claim 1, wherein the water is removed from the aqueous lactose solution by cooling to a temperature that lies 1-20° C. below the eutectic temperature of the aqueous mixture.

4. The method according to claim 1, wherein the crystallization of the lactose in (b) is conducted at a temperature of at least 0° C.

5. The method according to claim 1, wherein the concentration of the aqueous lactose solution in (a) is conducted at a temperature below −1° C. and the crystallization step is conducted at a temperature of at least 0° C.

6. The method according to claim 1, wherein the concentration of the aqueous lactose solution in (a) is conducted to obtain a concentrated solution having a lactose concentration of at least 15 wt. %.

7. The method according to claim 1, wherein the method is a continuous method.

8. The method according to claim 1, wherein the aqueous lactose solution originates from a whey permeate obtained by filtration of whey.

9. The method according to claim 1, wherein more than 99.9 wt. % of lactose is in dissolved form during the concentration of the aqueous lactose solution in (a).

10. The method according to claim 1, wherein the concentration of the aqueous lactose solution in (a) is a eutectic freeze crystallization step.

11. The method according to claim 1, comprising an isolation step, wherein the lactose crystals formed in the crystallization step are separated from the remaining lactose solution.

12. The method according to claim 1, wherein the water is removed from the aqueous lactose solution at a lactose concentration higher than 25 wt. % based on the total weight of the aqueous solution.

13. The method according to claim 1, wherein the water is removed from the aqueous lactose solution by cooling to a temperature that lies 1-15° C. below the eutectic temperature of the aqueous mixture.

14. The method according to claim 1, wherein the water is removed from the aqueous lactose solution by cooling to a temperature that lies 2-10° C. below the eutectic temperature of the aqueous mixture.

15. The method according to claim 1, wherein the concentration of the aqueous lactose solution in (a) is conducted to obtain a concentrated solution having a lactose concentration of at least 20 wt. %.

* * * * *